Figure 1A:
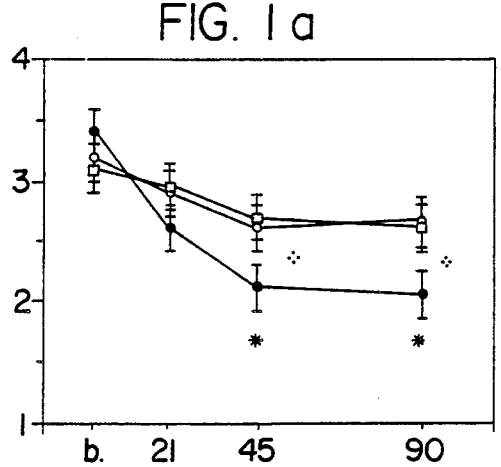
Figure 1B:
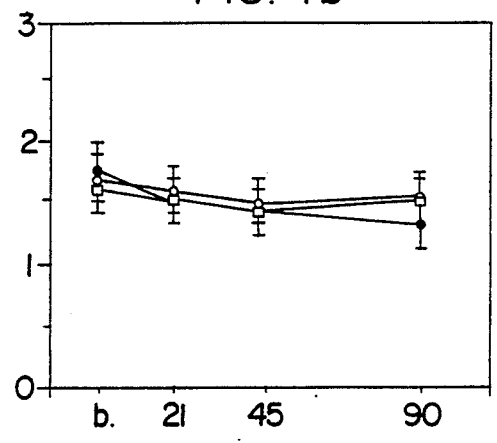
Figure 1C:
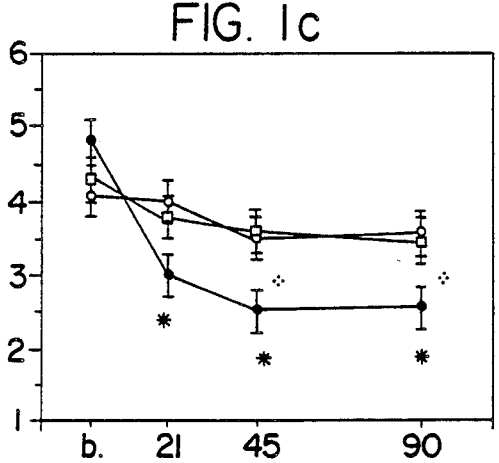
Figure 1D:
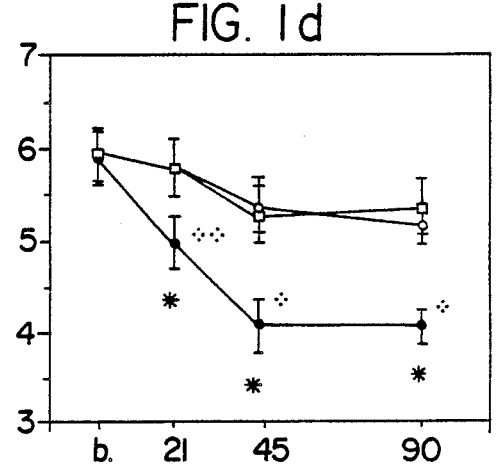

United States Patent [19]

Le Grazie

[11] Patent Number: 5,059,595

[45] Date of Patent: Oct. 22, 1991

[54] PHARMACEUTICAL COMPOSITIONS CONTAINING 5-METHYLTETRAHYDROFOLIC ACID, 5-FORMYLTETRAHYDROFOLIC ACID AND THEIR PHARMACEUTICALLY ACCEPTABLE SALTS IN CONTROLLED-RELEASE FORM ACTIVE IN THE THERAPY OF ORGANIC MENTAL DISTURBANCES

[75] Inventor: Cristina Le Grazie, Milan, Italy

[73] Assignee: Bioresearch, S.p.A., Milan, Italy

[21] Appl. No.: 496,366

[22] Filed: Mar. 20, 1990

[30] Foreign Application Priority Data

Mar. 22, 1989 [IT] Italy ..................... 19867 A89

[51] Int. Cl.⁵ .................. A61K 9/22; A61K 31/505
[52] U.S. Cl. .................. 424/468; 424/469; 424/470; 514/269
[58] Field of Search .......... 544/255, 261; 514/269; 424/468, 469, 470

[56] References Cited

U.S. PATENT DOCUMENTS

| | | | |
|---|---|---|---|
| 4,369,172 | 1/1983 | Schor et al. | 424/430 |
| 4,372,957 | 2/1983 | Duch et al. | 514/258 |
| 4,585,652 | 4/1986 | Miller et al. | 424/83 |
| 4,619,913 | 10/1986 | Luck et al. | 514/802 |
| 4,766,149 | 8/1988 | Osswald et al. | 514/553 |
| 4,812,449 | 3/1989 | Rideout | 514/183 |
| 4,818,759 | 4/1989 | Charping | 514/260 |
| 4,826,817 | 5/1989 | Brown et al. | 514/19 |
| 4,880,812 | 11/1989 | Kelley | 514/272 |
| 4,897,395 | 1/1990 | Duch et al. | 514/258 |
| 4,921,836 | 5/1990 | Bigham et al. | 514/19 |
| 4,940,713 | 7/1990 | Kelley | 514/272 |
| 4,952,402 | 8/1990 | Sparks et al. | 424/470 |

FOREIGN PATENT DOCUMENTS

| | | |
|---|---|---|
| 0164964 | 3/1985 | European Pat. Off. . |
| 0290819 | 4/1988 | European Pat. Off. . |
| 1572137 | 2/1977 | United Kingdom . |
| 2072504 | 10/1981 | United Kingdom . |

OTHER PUBLICATIONS

Periti et al., CA. 99: 205503g (1983).
Taguchi et al., CA. 95: 161754a (1981).
Whitehead et al., CA. 86: 115088c (1977).
Perry, CA. 73: 33827k (1970).
Rote Liste, 1985, no. 12023.

*Primary Examiner*—Shep K. Rose
*Attorney, Agent, or Firm*—Birch, Stewart, Kolasch & Birch

[57] ABSTRACT

This invention relates to pharmaceutical compositions containing 5-methyltetrahydrofolic acid, 5-formyltetrahydrofolic acid and their pharmaceutical acceptable salts in controlled-release form which are active in the therapy of organic mental disturbances and in particular in the treatment of senile and presenile primary degenerative dementia of Alzheimer type and multiinfarctual dementia.

7 Claims, 8 Drawing Sheets

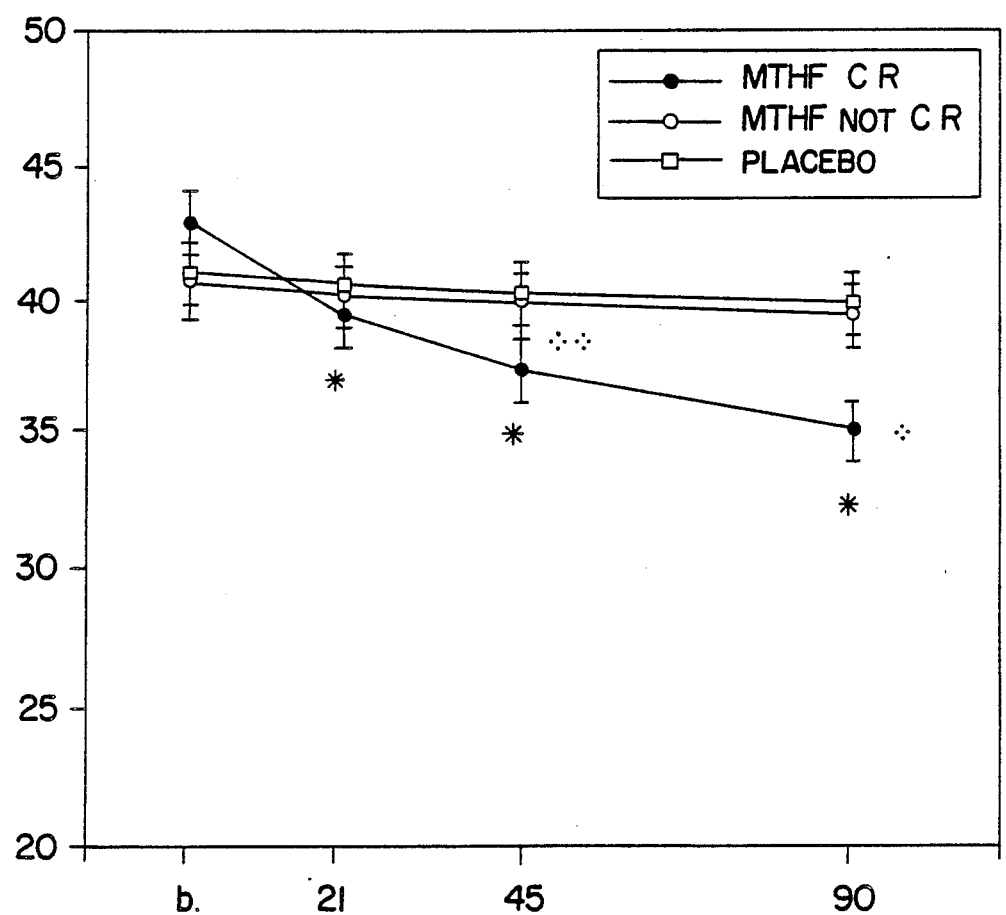

✳ COMPARISON IN THE GROUP VS BASAL P<0.01

✧ COMPARISON VS PLACEBO AND VS MTHF NOT C R P<0.01

∗ COMPARISION IN THE GROUP VS BASAL P<0.01

∴ COMPARISION VS PLACEBO AND VS MTHF NOT C R P<0.01

✳ COMPARISON IN THE GROUP VS BASAL P<0.0.1

⋰ COMPARISON VS PLACEBO AND VS MTHF NOT C R P<0.01

⋱⋰ COMPARISON VS PLACEBO AND VS MTHF NOT C R P<0.05

- ● — MTHF C R
- ○ — MTHF NOT C R
- □ — PLACEBO

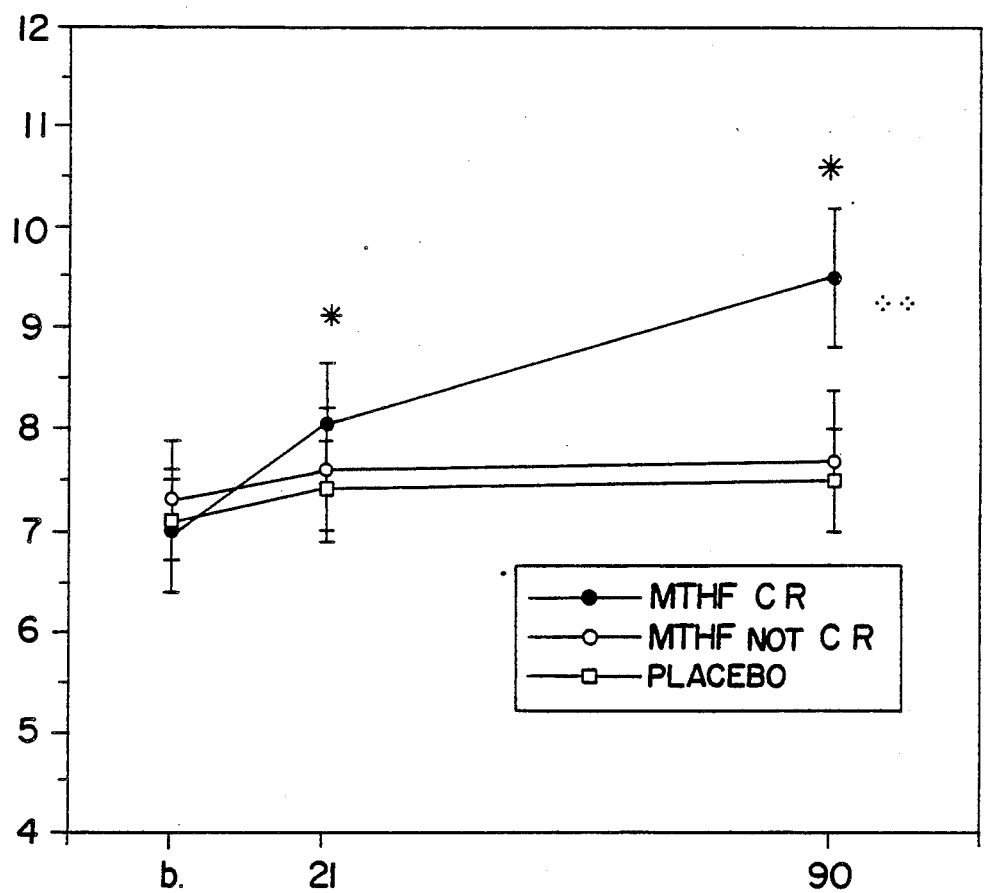

* COMPARISON IN THE GROUP VS BASAL $P<0.01$

∴ COMPARISON VS PLACEBO AND VS MTHF NOT C R $P<0.01$

∴∴ COMPARISON VS PLACEBO AND VS MTHF NOT C R $P<0.05$

- ●— MTHF C R
- ○— MTHF NOT C R
- □— PLACEBO

PHARMACEUTICAL COMPOSITIONS CONTAINING 5-METHYLTETRAHYDROFOLIC ACID, 5-FORMYLTETRAHYDROFOLIC ACID AND THEIR PHARMACEUTICALLY ACCEPTABLE SALTS IN CONTROLLED-RELEASE FORM ACTIVE IN THE THERAPY OF ORGANIC MENTAL DISTURBANCES

This invention relates to pharmaceutical compositions containing 5-methyltetrahydrofolic acid (MTHF), 5-formyltetrahydrofolic acid (FTHF) and their pharmaceutically acceptable salts in the preparation of pharmaceutical compositions in controlled-release form active in the therapy of organic mental disturbances.

In particular, the pharmaceutical compositions according to the present invention are active in the treatment of senile and presenile primary degenerative dementia of Alzheimer type and in the treatment of multiinfarctual dementia.

In the present text, for greater clarity and simplicity, the expression 5-methyltetrahydrofolic acid and the initials MTHF refer to compounds having the following complete chemical denomination: ($\pm$)-L-5-methyl-5,6,7,8-tetrahydrofolic acid and ($-$)-L-5-methyl-5,6,7,8-tetrahydrofolic acid and their salts, whereas the expression 5-formyltetrahydrofolic acid and the initials FTHF refer to compounds having the following complete chemical denomination: ($\pm$)-L-5-formyl-5,6,7,8-tetrahydrofolic acid and ($-$)-L-5-formyl-5,6,7,8-tetrahydrofolic acid and their salts.

No effective treatment is currently available in the therapy of organic mental disturbances, and in the particular case of dementia of Alzheimer type the drugs currently under study are still far from being unequivocally considered active (Davis K. L., Mohs R. C.: Cholinergic drugs in Alzheimer's disease; New Engl. J. Med. 315: 1286–7, 1986).

With regard to the numerous drugs used to treat the so-called "senile brain", their effectiveness has up to the present time been evaluated more in terms of the modifications induced by the drug in the cerebral flow and in the electroencephalogram, rather than in terms of clinical response. It has therefore not been established whether these physiological variations correspond to a real improvement in the elderly patient.

5-methyltetrahydrofolic acid, 5-formyltetrahydrofolic acid and their salts are a group of substances pertaining to the vitamin B complex, structurally related to pteroylglutamic acid (folic acid). This acid, which is not synthesized by the cells of mammals, is of particular biological importance because it intervenes in a series of chemical reactions involving transfer of monocarbon groups and in particular in the synthesis of the purine ring and thymidylate and in the neogenesis of methyl groups. In the circulating blood the folate pool is mostly represented by MTHF, but also by FTHF. MTHF represents the main form of folate transport in the blood. At the choroid plexus level it passes from the blood to the body fluid and from here, by passive diffusion, into the tissue and nerve cells. In the central nervous system the folates and in particular MTHF participate in basic biochemical processes by intervening in the synthesis of S-adenosyl-L-methionine (SAMe), in the metabolism of certain aminoacids (glycine, serine, glutamic acid), in the nodulatory activity of monoaminergic transmission systems (noradrenaline, serotonin, dopamine), in nucleic acid synthesis and in ATP and GTP production.

The therapeutic use of folic acid and its cofactors has up to the present time been limited to the prevention and treatment of body deficiencies of this vitamin, i.e. to the treatment of hypofolatemic subjects.

The object of the present invention is to allow effective therapy of organic mental disturbances by providing pharmaceutical compositions which possess demonstrated clinical effectiveness in the therapy of such disturbances and are free of side effects.

We have now surprisingly found that pharmaceutical compositions of controlled-release type, with an active principle release time varying from 15 minutes to 8 hours and preferably varying from 20 to 60 minutes, and containing from 5 to 200 mg and preferably from 10 to 50 mg of MTHF or FTHF or their pharmaceutically acceptable salts, demonstrate unexpected pharmacological properties when used to treat subjects affected by organic mental disturbances.

The organic mental disturbances are diagnosed on the basis of criteria contained in the Diagnostic and Statistical Manual of Mental Disorders, Third Edition Revised (DSM-III-R), published by the American Psychiatric Association in 1987. This manual describes organic mental disturbances according to the following codes:

290.21 Senile primary degenerative dementia of Alzheimer type with depression;

290.13 Presenile primary degenerative dementia of Alzheimer type with depression;

290.43 Multiinfarctual dementia with depression.

According to the definition given to it by Stone in the American Psychiatric Glossary (Am. Psych. Press, Washington, 6th Edition, 1988 p. 46), dementia is "an organic mental illness in which there is deterioration of previously acquired intellectual capacity, this deterioration being of sufficient severity to interfere with work or social activities. The most important symptom is memory disturbance. In addition abstract though, capacity for judgement and control of impulses are compromised, and/or there is personality change. Dementia can be progressive, stationary or reversible depending on the morbid symptoms and on the availability of effective treatment". The diagnostic criteria for dementia are given in Table 1, taken from DMS-III-R.

TABLE 1

DIAGNOSTIC CRITERIA FOR DEMENTIA

A. Loss of intellectual faculties to such an extent as to interfere with social or professional activities.

B. Memory deficit.

C. At least one of the following elements:
  1) deficit of abstract thought, encountered in literal interpretation of proverbs, in incapacity to recognise similarities and differences between related words, in difficulty in defining words and concepts, and in other similar tests;
  2) deficit of critical judgement;
  3) other disturbances of the higher cortical functions, such as aphasia (language disturbance related to cerebral malfunction), apraxia (inability to execute motor activities notwithstanding soundness of comprehension and motricity), agnosia (inability to recognise or identify objects notwithstanding soundness of sensitive functions), "constructive apraxia" (such as inability to copy three-dimensional figures and put blocks together, or to arrange sticks in predetermined designs);

4) personality changes, such as alteration or accentuation of premorbid states.

D. Absence of obnubilation of consciousness i.e. lack of response to the diagnostic criteria for Delirium or Intoxication, although these symptoms may mutually superimpose).

E. One of the following elements:
   1) demonstration of a specific organic factor etiologically related to the disturbance, on the basis of anamnesis, clinical examination or laboratory examinations;
   2) in the absence of such demonstration, presumption of an organic factor necessary for development of the syndrome, when there are proper reasons for excluding situations other than organic mental disturbances, and when the behavioural alteration is represented by an intellectual deficit in different areas.

The characteristics and advantages of the present invention will be more apparent from the summary description of a significant clinical trial selected from those carried out using the compositions according to the present invention.

CLINICAL TRIAL

The purpose of this trial was to verify the therapeutic effects of prolonged administration of controlled-release MTHF compared with the administration of MTHF not in controlled-release form and of a placebo to elderly subjects affected by organic mental disturbances with depression of mood in accordance with the definitions given in DSM-III-R. This was a multi-centre perspective randomized trial of double-blind controlled type. The trial was carried out in 7 centres, each of which involved 30 patients giving a total of 210 patients. The patients were divided randomly into three sub-groups, these receiving MTHF in controlled-release form, MTHF not in controlled-release form and placebo respectively.

On the basis of inclusion criteria patients of both sexes 65 years of age and over, institutionalised for at least 3 months, took part. The patients had to have shown evident clinical signs of cerebral deterioration for at least one year. In particular, the presence of at least 3 of the following symptoms was required: mental confusion with compromised cognition, absence or reduction of appetite, ease of exhaustion, fear, irritability, impulsiveness, absence of cooperation, emotive weakness, poor sociability, anxiety and depression. The criteria for admission were a point score of between 10 and 24 on the MMSE (Mini Mental State Examination) scale and a point score of 18 or more on the Hamilton depression scale (HAM-D).

The criteria for exclusion were represented by: age less than 65 years, MMSE point score less than 10 or greater than 24, HAM-D point score less than 18, presence of serious cardiovascular, renal, respiratory, hepatic, dismetabolic, hematological or neoplastic pathology. The following patients were also excluded: those with anamnesis of epilepsy or convulsive manifestations, those with Parkinson's disease at stages III, IV or V, those with self-wounding tendencies, those with brain damage of traumatic or infective origin, and those with functional psychosis. Also excluded were those patients under treatment with drugs which could interfere with the results of the present research. After a wash-out period of 15 days in which all pharmacological treatment for the pathology under examination was suspended, the patients taking part were assigned in a consecutive and random manner to the treatment, which was carried out over the scheduled period of 90 days. The MTHF in controlled-release form (average release time 1 hour) was administered orally at a dose of 50 mg/day in a single administration, the MTHF not in controlled-release form was administered orally at a dose of 50 mg/day in a single administration, and the placebo likewise.

To evaluate the effects of the treatment certain psychiatric scales particularly suitable for investigating behaviour, autonomy and depressed humour were used. The evaluation scales used were as follows:

1) Geriatric Rating Scale (GRS) of Plutchik (Plutchik et al., J. Amer. Geriatric Soc., 1970, 18: 491) which evaluates the alterations in the physical, mental and social state which influence daily living, i.e. the self-sufficiency and behaviour of the patient. This scale comprises 31 items graduated from 0 (normal) to 2 (serious). Mostly, these items are combined into symptom groups in relation to the aspects to be explored. Thus self-sufficiency combines 6 items, sleep disturbance 3, global deficit 5, initiative 4, and agressivity and sociability 6.

2) Dementia Rating Scale (DRS) of Gottfries (Gottfries et al., Clin. Neuropharmacol., 1984, 7/1: 12) with 26 items graduated from 0 to 6 indicating increasing severity of the syndrome. It is divided into the following 4 sections, which evaluate:
   a) psychiatric symptoms (confusion, irritability, anxiety, distress, depression of humour, restlessness;
   b) emotion;
   c) bodily movement,
   d) mental functions (memory, attention, vigilance).

3) Hamilton depression evaluation scale (HAM-D) with 21 items (Hamilton, British J. Med. Psychol., 1959, 32: 50).

Evaluation of the individual parameters of the aforesaid scales was done before commencement of treatment (basal value) and after 21, 45 and 90 days of therapy (T21, T45 and T90).

The following psychometric tests were used to evaluate the individual state of performance:

1) Wechsler Adult Intelligence Scale Test (W.A.I.S.) (Wechsler, "Wechsler Adult Intelligence Scale Manual", Psychological Corporation, New York, 1955), which consists of reconstructing human figures divided into 5 segments.

2) Randt Memory Test (Randt et al., Clin. Neuropsychol., 1980, 2: 184) limited to the acquisition and repeating of 5 words; it allows evaluation both of any modifications in the various memory aspects and the effectiveness of pharmacological treatment on this function.

3) Toulouse-Pieron test (Andreoli et al., Il Fracastoro, 1975. 68/Suppl. No. 1-2: 71) for visual exploration.

4) Semantic Verbal Memory Test (Villardita, Intern. Neuropsychol. Soc. 7th Europ. Conference, Aachen, 13.06.1984) which consists of the immediate and deferred (20 minutes) recall of 15 frequently used words pertaining to 3 semantic categories.

5) Digit Span (Wechsler, "Wechsler Adult Intelligence Scale Manual", Psychological Corporation, New York, 1955), which consists of the forward and backward repeating of numbers of increasing length read to the patient by the examiner.

The psychometric tests were carried out before commencement of treatment (basal value) and after 21 and 90 days of treatment (T21 and T90). During the course (T21 and T45) and at the end (T90) of treatment the medical practitioner, with the cooperation of the patient's relatives and the paramedic personnel, expressed a global judgement on the effects of the therapy.

The variations in the individual parameters were evaluated during and at the end of the treatment, using variance analysis based on two evaluation criteria (drug and time), with multiple Tukey comparisons.

Having undergone the above selection procedure, 184 patients were available for evaluation divided as follows:
Group using MTHF in controlled-release form — 60
Group using MTHF not in controlled-release form — 62
Group using placebo — 62

The demographic and clinical characteristics of the patients are shown in Table 2, from which the similarity between the groups can be seen. The values in parentheses represent standard deviation (S.D.).

TABLE 2

| Characteristics of the 184 patients evaluated | | | |
|---|---|---|---|
| | MTHF controlled release 60 | MTHF not controlled release 62 | Placebo 62 |
| Sex M/F | 27/33 | 25/37 | 30/32 |
| Average age (years) | 74.6 | 75.3 | 73.9 |
| (S.D.) | (5.6) | (4.8) | (5.3) |
| Average weight (kg) | 63.6 | 62.7 | 59.8 |
| (S.D.) | (10.3) | (11.2) | (9.4) |
| Average illness duration (years) | 4.5 | 5.1 | 4.7 |
| (S.D.) | (7.2) | (8.2) | (8.4) |

In the figures cited below, the MTHF in controlled-release form is indicated by MTHF R C and the MTHF not in controlled-release form is indicated by MTHF non R C.

FIG. 1 shows the results obtained using the Plutchik geriatric evaluation scale (G.R.S.).

Figure 1E:
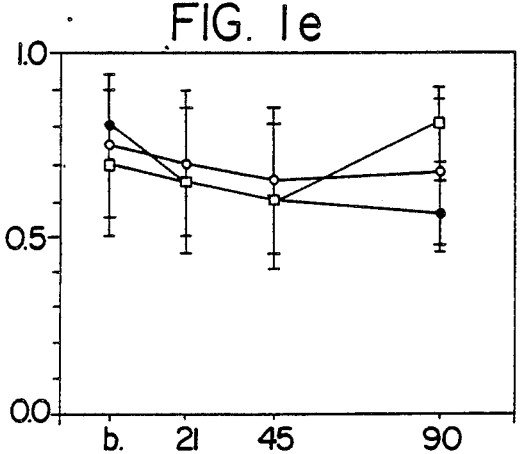

In FIGS. 1a to 1e the horizontal axis represents time in days and the vertical axis represents the average point score (± standard error) obtained on the Plutchik G.R.S. for the 3 groups of patients under treatment. The individual graphs represent the following items: self-sufficiency (FIG. 1a), sleep disturbance (FIG. 1b), global deficit (FIG. 1c), initiative (FIG. 1d) and unadaptable behaviour (FIG. 1e).

It can be seen that whereas the groups of patients treated with MTHF not in controlled-release form or with placebo show no significant difference from the basal values at T0 (b) and at the end of treatment (T90), the group of patients treated with MTHF in controlled-release form shows a statistically significant difference even at T21 for the global deficit (FIG. 1c) and for initiative (FIG. 1d), and at T45 for self-sufficiency. In contrast, sleep disturbance (FIG. 1b) and unadaptable behaviour (FIG. 1e) show no significant differences after the treatment period compared with the basal values. Analysis of the variance shows the existence of interaction between treatment and time ($p < 0.01$) for the above parameters with statistically significant difference.

FIG. 2 shows the results obtained using the Gottfries Dementia Scale Rating (DRS) in which the horizontal axis represents time in days and the vertical axis represents the average point score (± standard error), the results being clearly most apparent in the group receiving MTHF in controlled-release form. By T45 there is a significant difference compared with the treatments with placebo and MTHF not in controlled-release form ($p < 0.05$), this difference increasing further by T90 ($p < 0.01$).

Figure 3:
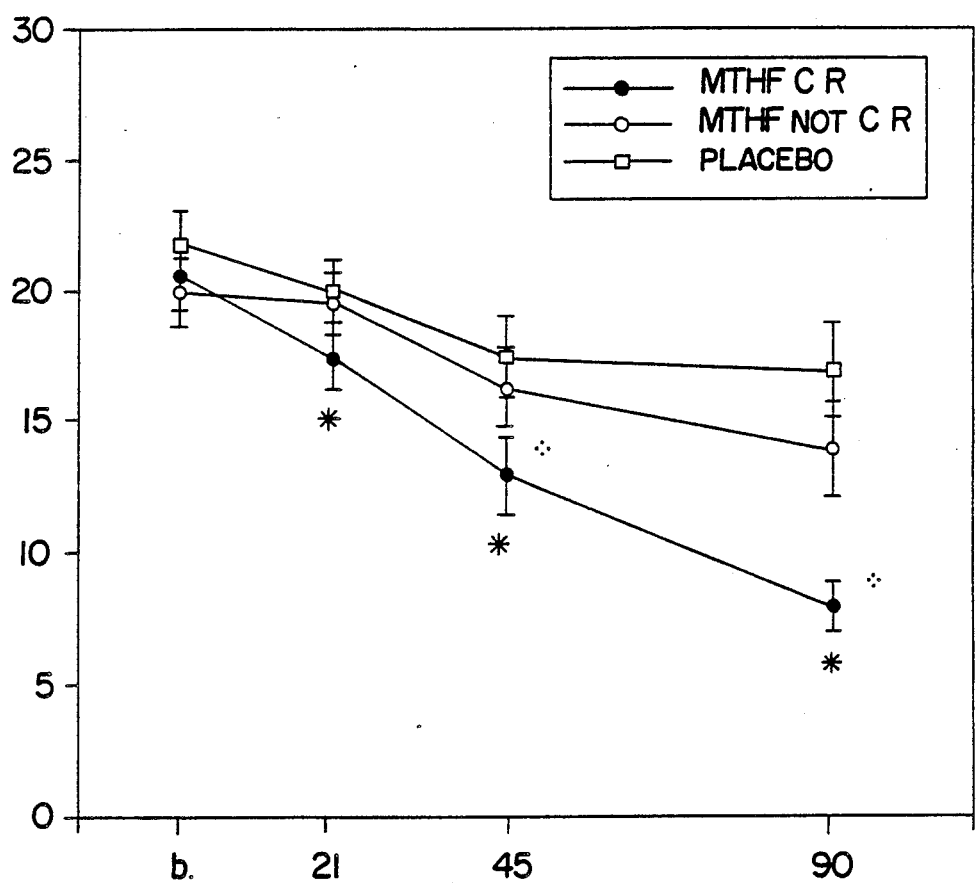
Figure 4:
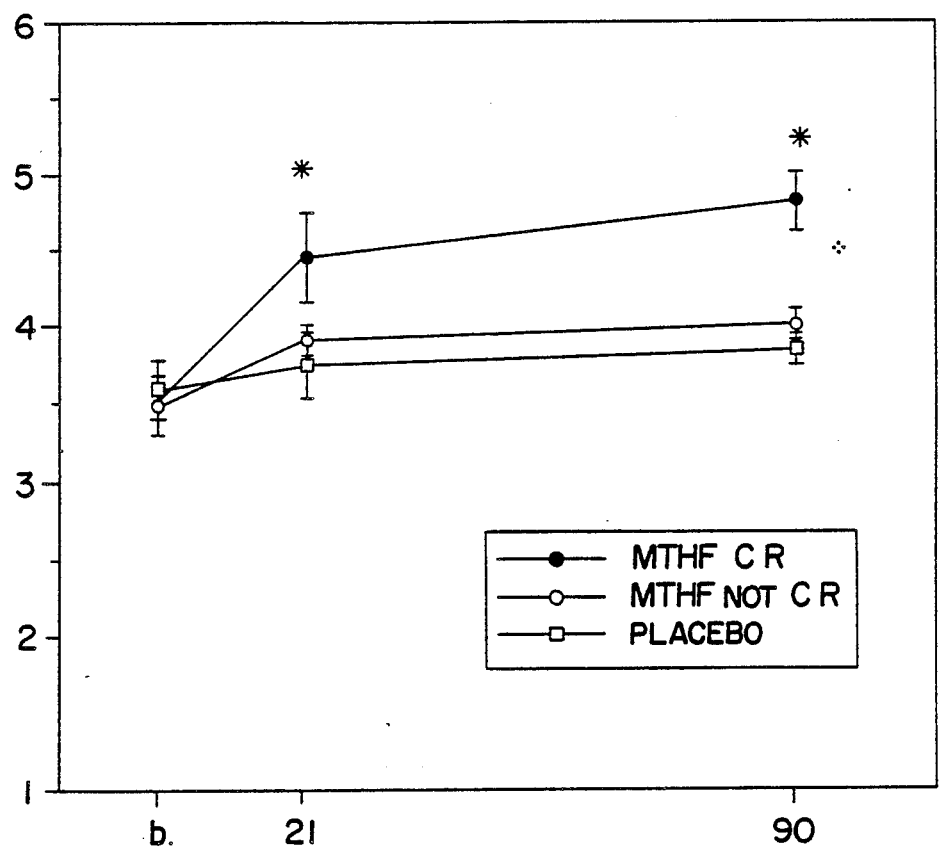
Figure 5A:
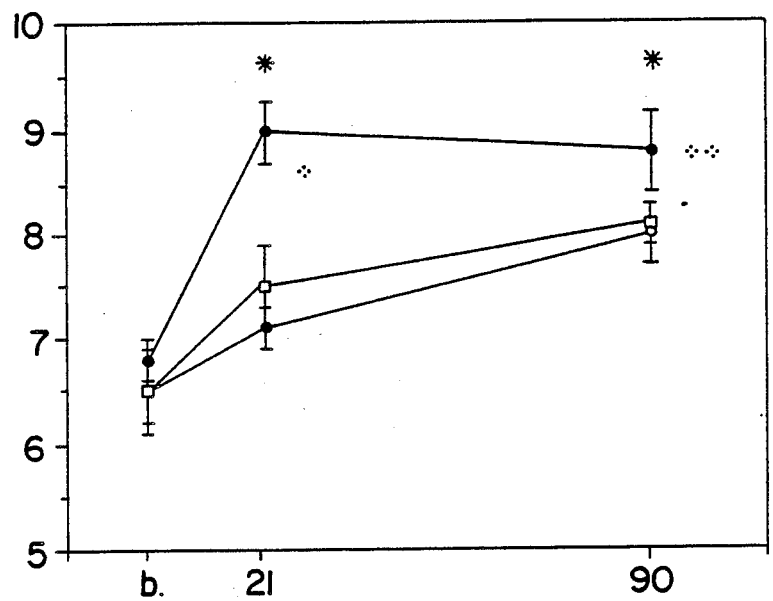
Figure 5B:
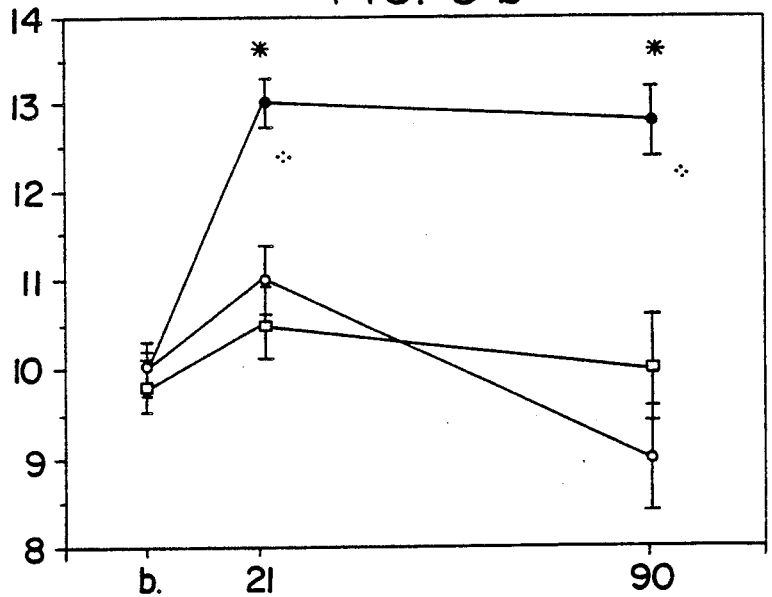
Figure 6:
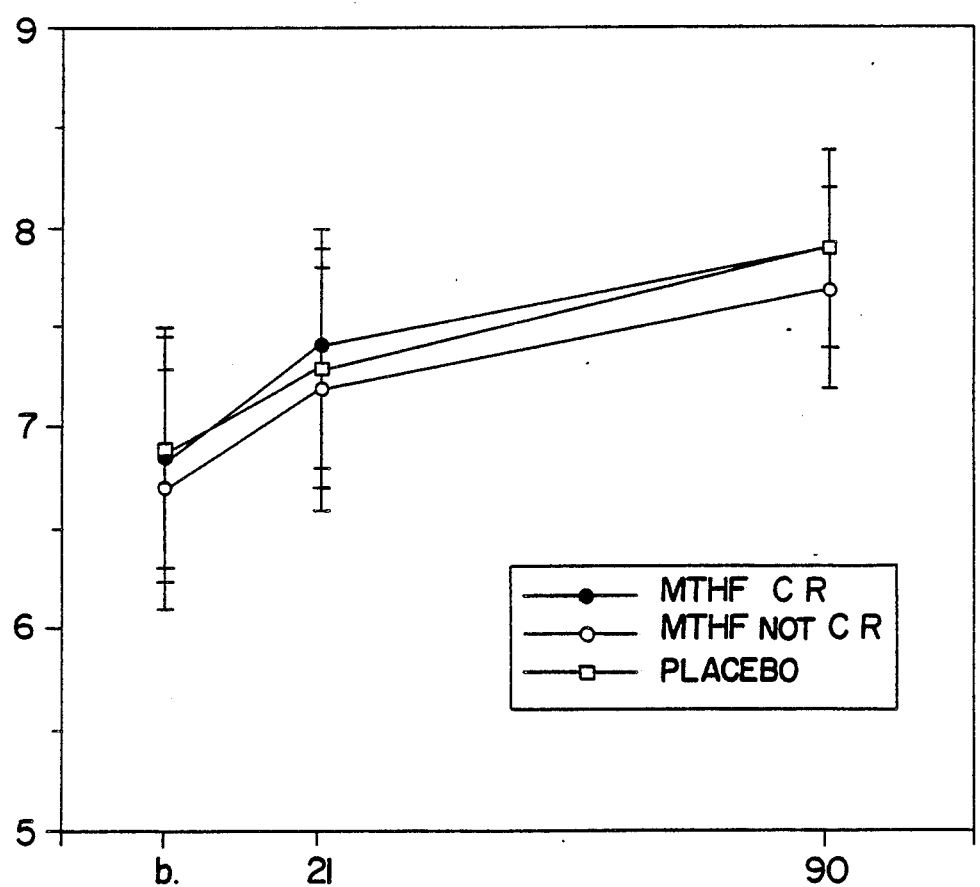

FIG. 3 shows the results obtained using the Hamilton Rating Scale (HAM-D) for depression, the horizontal axis representing time in days and the vertical axis the average point score (± standard error). Treatment with MTHF in controlled-release form acts on temperament to clearly improve depressive symptomatology from T21. At the end of treatment (T90) the average point score on the HAM-D scale, equal to 20.3 in the basal evaluation, passes to 8.3, corresponding to an improvement of 59.1%, which is decidedly better ($p < 0/01$) than that obtained with MTHF not in controlled-release form (23.0%) or with placebo (22.2%).

FIGS. 4 to 8 show the results obtained for all the psychometric tests used, namely: W.A.I.S. test (FIG. 4), Randt memory test for word acquisition (FIG. 5a), Randt memory test for word repetition (FIG. 5b), Toulouse-Pieron test (FIG. 6), semantic verbal memory test (FIG. 7), digit span for forward test (FIG. 8a) and digit span for backward test (FIG. 8b).

Figure 8A:
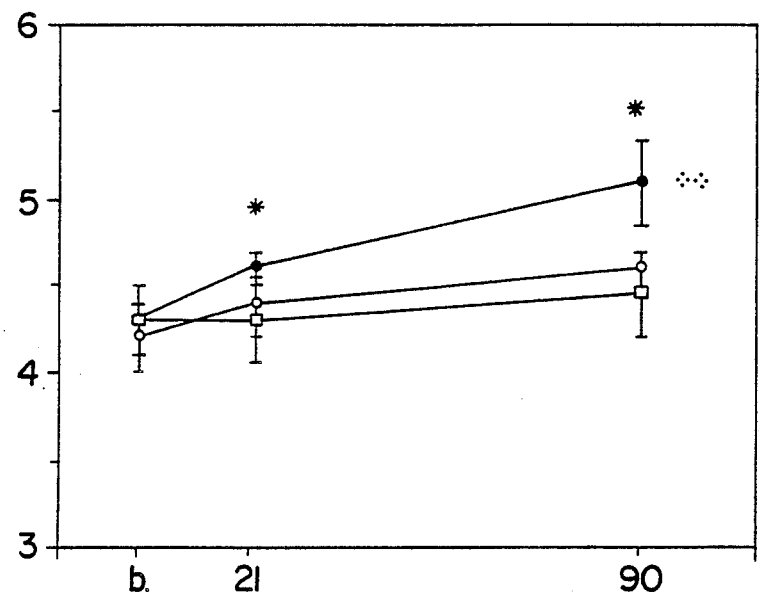
Figure 8B:
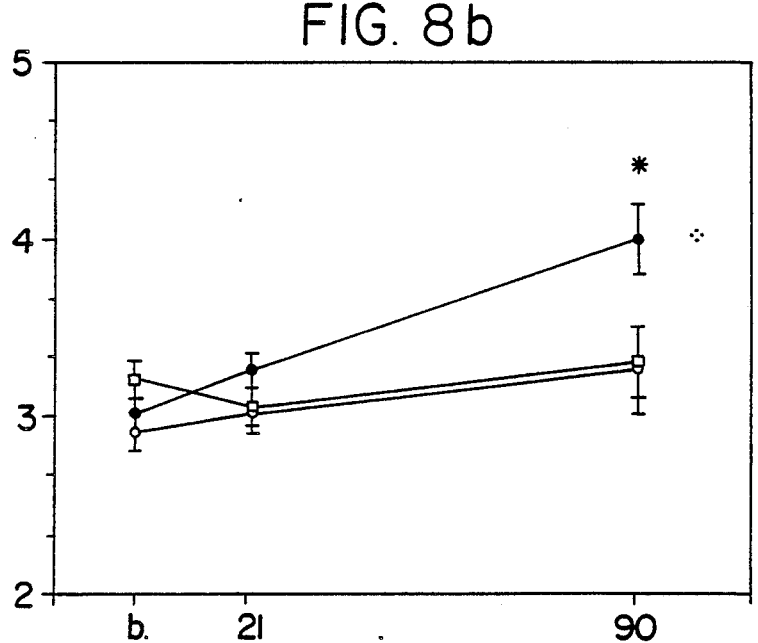

All the psychometric tests with the exception of the Toulouse-Pieron test (FIG. 6) showed statistically significant improvements for treatment with MTHF in controlled-release form ($p < 0.05$) according to the present invention. In particular at T21 there was a statistically significant difference for the W.A.I.S. test (FIG. 4), the Randt memory test (FIG. 5), the semantic verbal memory test (FIG. 7) and the digit span for the forward test (FIG. 8a), and at T90 in the case of the digit span for the backward test (FIG. 8b). In contrast, the group of patients treated with MTHF not in controlled-release form and with placebo showed no modifications of any kind.

Tolerance during the treatment was good for nearly all patients, with the exception of two patients of the MTHF controlled-release group, who complained of slight cephalea during the initial days of treatment. This condition subsequently spontaneously disappeared, although drug administration continued.

Table 3 shows the global judgement, expressed by the medical practitioner who performed the therapy, on the effectiveness of the treatment at T21, T45 and T90. In formulating this judgement the practitioner also consulted the patient's relatives and the paramedic personnel. The greater number of positive replies for treatment with MTHF in controlled-release form was statistically significant by T45 and further increased until T90 when 60% of the patients were recognised as and declared to be improved, against 24% of the patients in the group using MTHF not in controlled-release form and 26% in the placebo group.

TABLE 3
GLOBAL JUDGEMENT ON THE TREATMENT EFFECTIVENESS

| | WORSENED | UNCHANGED | IMPROVED | MUCH IMPROVED | TOTAL |
|---|---|---|---|---|---|
| *Time 21 days* | | | | | |
| MTHF in controlled-release form: | 5 | 35 | 18 | 2 | 60 |
| MTHF not in controlled-release form: | 6 | 45 | 9 | 2 | 62 |
| placebo: | 10 | 40 | 10 | 2 not significant | 62 |
| *Time 45 days* | | | | | |
| MTHF in controlled-release form: | 4 | 29 | 22 | 5 | 60 |
| MTHF not in controlled-release form: | 6 | 44 | 10 | 2 | 62 |
| placebo: | 7 | 42 | 11 | 2 P = 0.05 | 62 |
| *Time 90 days* | | | | | |
| MTHF in controlled-release form: | 2 | 22 | 28 | 8 | 60 |
| MTHF not in controlled-release form: | 4 | 43 | 12 | 3 | 62 |
| placebo: | 6 | 40 | 14 | 2 P = 0.001 | 62 |

Analogous experiments were conducted using pharmaceutical compositions according to the present invention containing different doses of MTHF and FTHF in controlled-release form, namely 5 mg (20 patients), 15 mg (20 patients), 20 mg (20 patients), 25 mg (15 patients), 40 mg (20 patients), 100 mg (20 patients) and 200 mg (20 patients), it being found that these doses also produce positive effects on the parameters analyzed.

The pharmaceutical compositions obtained using MTHF, FTHF and their salts, in raceme or optically active form, according to the invention, do not interfere with the sleeping/waking cycle, do not produce sedation, do not produce dependence or inurement and in general do not produce side effects.

Some examples of pharmaceutical compositions according to the present invention are given hereinafter for the sole purpose of non-limiting illustration.

EXAMPLE 1

Gastro-resistant controlled-release tablet containing 10 mg of MTHF; release time = 15 or 20 minutes.

| 1 tablet contains: | |
|---|---|
| MTHF calcium pentahydrate salt (equivalent to 10 mg MTHF) | 12.6 mg |
| Pregelatinized starch | 115.0 mg |
| Lactose 100 mesh | 72.7 mg |
| Hydroxypropylmethylcellulose | 5.0 mg |
| Magnesium stearate | 1.0 mg |
| Cellulose acetophthalate | 7.5 mg |
| Diethylphthalate | 2.5 mg |

EXAMPLE 2

Gastro-resistant controlled-release tablet containing 15 mg of MTHF; release time = 20 or 30 minutes.

| 1 tablet contains: | |
|---|---|
| MTHF calcium pentahydrate salt (equivalent to 15 mg MTHF) | 18.8 mg |
| Pregelatinized starch | 115.0 mg |
| Lactose 100 mesh | 60.2 mg |
| Hydroxypropylmethylcellulose | 5.0 mg |
| Magnesium stearate | 1.0 mg |
| Cellulose acetophthalate | 7.5 mg |
| Diethylphthalate | 2.5 mg |

EXAMPLE 3

Gastro-resistant controlled-release tablet containing 20 mg of MTHF; release time = 30 or 35 minutes.

| 1 tablet contains: | |
|---|---|
| MTHF calcium pentahydrate salt (equivalent to 20 mg MTHF) | 25.1 mg |
| Microcrystalline cellulose | 80.0 mg |
| Lactose 100 mesh | 79.9 mg |
| Hydroxypropylmethylcellulose | 10.0 mg |
| Glyceryl behenate | 5.0 mg |
| Cellulose acetophthalate | 7.5 mg |
| Diethylphthalate | 2.5 mg |

EXAMPLE 4

Gastro-resistant controlled-release tablet containing 25 mg of MTHF; release time = 35 or 40 minutes.

| 1 tablet contains: | |
|---|---|
| MTHF calcium pentahydrate salt (equivalent to 25 mg MTHF) | 31.6 mg |
| Microcrystalline cellulose | 80.0 mg |
| Lactose 100 mesh | 73.4 mg |
| Hydroxypropylmethylcellulose | 10.0 mg |
| Glyceryl behenate | 5.0 mg |
| Cellulose acetophthalate | 7.5 mg |

-continued

| 1 tablet contains: | |
|---|---|
| Diethylphthalate | 2.5 mg |

EXAMPLE 5

Gastro-resistant controlled-release tablet containing 40 mg of MTHF; release time = 50 or 60 minutes.

| 1 tablet contains: | |
|---|---|
| MTHF calcium pentahydrate salt (equivalent to 40 mg MTHF) | 50.6 mg |
| Microcrystalline cellulose | 80.0 mg |
| Lactose 100 mesh | 54.4 mg |
| Hydroxypropylmethylcellulose | 10.0 mg |
| Glyceryl behenate | 5.0 mg |
| Cellulose acetophthalate | 7.5 mg |
| Diethylphthalate | 2.5 mg |

EXAMPLE 6

Gastro-resistant controlled-release tablet containing 50 mg of MTHF; release time = 60 minutes.

| 1 tablet contains: | |
|---|---|
| MTHF calcium pentahydrate salt (equivalent to 50 mg MTHF) | 63.2 mg |
| Microcrystalline cellulose | 80.0 mg |
| Lactose 100 mesh | 41.7 mg |
| Hydroxypropylmethylcellulose | 10.0 mg |
| Glyceryl behenate | 5.0 mg |
| Cellulose acetophthalate | 7.5 mg |
| Diethylphthalate | 2.5 mg |

EXAMPLE 7

Gastro-resistant controlled-release tablet containing 50 mg of FTHF; release time = 60 minutes.

| 1 tablet contains: | |
|---|---|
| FTHF calcium pentahydrate salt (equivalent to 100 mg FTHF) | 66.7 mg |
| Carboxyvinylpolymer | 20.0 mg |
| Microcrystalline cellulose | 112.3 mg |
| Magnesium stearate | 1.0 mg |
| Cellulose acetophthalate | 7.5 mg |
| Diethylphthalate | 2.5 mg |

EXAMPLE 8

Gastro-resistant controlled-release tablet containing 100 mg of MTHF; release time = 90 or 120 minutes.

| 1 tablet contains: | |
|---|---|
| MTHF calcium pentahydrate salt (equivalent to 100 mg MTHF) | 126.5 mg |
| Dibasic calcium phosphate | 90.0 mg |
| Lactose 100 mesh | 163.0 mg |
| Hydroxypropylmethylcellulose | 15.0 mg |
| Magnesium stearate | 5.5 mg |
| Cellulose acetophthalate | 15.5 mg |
| Diethylphthalate | 5.0 mg |

EXAMPLE 9

Gastro-resistant controlled-release tablet containing 200 mg of MTHF; release time = 180 or 210 or 240 minutes.

| 1 tablet contains: | |
|---|---|
| MTHF calcium pentahydrate salt (equivalent to 200 mg MTHF) | 251.0 mg |
| Hydroxypropylmethylcellulose | 30.0 mg |
| Lactose 100 mesh | 149.0 mg |
| Glyceryl behenate | 5.5 mg |
| Cellulose acetophthalate | 15.0 mg |
| Diethylphthalate | 5.0 mg |

EXAMPLE 10

Gastro-resistant controlled-release tablet containing 200 mg of FTHF; release time = 4 hours.

| 1 tablet contains: | |
|---|---|
| FTHF calcium pentahydrate salt (equivalent to 200 mg MTHF) | 266.7 mg |
| Microcrystalline cellulose | 63.3 mg |
| Hydrogenated castor oil | 100.0 mg |
| Glyceryl behenate | 20.0 mg |
| Cellulose acetophthalate | 15.0 mg |
| Diethylphthalate | 5.0 mg |

EXAMPLE 11

Controlled-release suppository containing 50 mg of MTHF.

| 1 suppository contains: | |
|---|---|
| MTHF calcium pentahydrate salt (equivalent to 50 mg MTHF) | 63.2 mg |
| Hydroxypropylmethylcellulose | 50.0 mg |
| Semisynthetic glycerides | 1886.8 mg |

EXAMPLE 12

Controlled-release injectable form containing 50 mg of MTHF.

| 1 vial contains: | |
|---|---|
| MTHF calcium pentahydrate salt (equivalent to 50 mg MTHF) | 63.2 mg |
| Glutathione | 10.0 mg |
| Citric acid | 30.0 mg |
| Hydroxyethylcellulose | 10.0 mg |
| Mannitol | 160.0 mg |
| Methyl p-hydroxybenzoate | 1.0 mg |
| Sodium hydroxide | 17.7 mg |
| Water for injectable preparations | to make up to 3 ml |

EXAMPLE 13

Controlled-release transdermic system containing 20 mg of MTHF

| 1 transdermic system contains: | |
|---|---|
| MTHF calcium pentahydrate salt (equivalent to 20 mg MTHF) | 25.1 mg |
| Fluid silicone | 174.8 mg |
| Precipitated silica | 15.2 mg |

EXAMPLE 14

Controlled-release transdermic system containing 50 mg of MTHF

| 1 transdermic system contains: | |
| --- | --- |
| MTHF calcium pentahydrate salt (equivalent to 50 mg MTHF) | 63.3 mg |
| Glycerin | 135.0 mg |
| Polyvinyl alcohol | 7.5 mg |
| Polyvinylpyrrolidone | 5.0 mg |
| Citric acid | 2.5 mg |
| Purified water | 100.0 mg |

The present invention is susceptible to numerous modifications all falling within the inventive concept, and in addition all details can be replaced by others technically equivalent.

I claim:

1. In a therapeutic method for treating an elderly depressed patient diagnosed as having at least one organic mental disturbance selected from the group consisting of senile primary degenerative dementia of the Alzheimer type with depression, presenile primary degenerative dementia of the Alzheimer type with depression, and multiinfarctual dementia with depression, the improvement, as compared to orally administering folate not in controlled-release form, or to placebo, consisting essentially of the step of orally administering a therapeutically effective amount of 5-methyl-tetrahydrofolic acid or 5-formyl-tetrahydrofolic acid or a pharmaceutically acceptable salt thereof in a controlled-release form.

2. The therapeutic method according to claim 1, wherein said 5-methyl-tetrahydrofolic acid or said 5-formyl-tetrahydrofolic acid is released within a time period of between 15 minutes and 8 hours.

3. A therapeutic method according to claim 1, wherein said 5-methyl-tetrahydrofolic acid or said 5-formyl-tetrahydrofolic acid is released within a time period of between 20 minutes and 60 minutes.

4. A therapeutic method according to claim 1, wherein said 5-methyl-tetrahydrofolic acid or said 5-formyl-tetrahydrofolic acid in controlled-release form is administered in amounts ranging from 5 to 200 mg per dose.

5. A therapeutic method according to claim 1, wherein said 5-methyl-tetrahydrofolic acid or said 5-formyl-tetrahydrofolic acid is administered in amounts ranging from 10 to 50 mg per dose.

6. A therapeutic method according to claim 1, wherein said 5-methyl-tetrahydrofolic acid or said 5-formyl-tetrahydrofolic acid is adminstered in gastrosoluble controlled-release form.

7. A therapeutic method according to claim 1, wherein said 5-methyl-tetrahydrofolic acid or said 5-formyl-tetrahydrofolic acid is administered in an enterosoluble controlled-release form.

* * * * *